United States Patent [19]

Clum et al.

[11] Patent Number: 4,663,156

[45] Date of Patent: May 5, 1987

[54] SUNSCREEN COMPOSITIONS

[75] Inventors: Charles E. Clum, Kingston; William V. Murray, Belle Mead; Elvin R. Lukenbach, Somerset, all of N.J.

[73] Assignee: Johnson & Johnson Baby Products Company, New Brunswick, N.J.

[21] Appl. No.: 702,703

[22] Filed: Feb. 19, 1985

Related U.S. Application Data

[63] Continuation-in-part of Ser. No. 375,072, May 5, 1982, Pat. No. 4,514,383.

[51] Int. Cl.$^4$ .......................... A61K 7/42; A61K 7/44
[52] U.S. Cl. ........................................ 424/59; 424/60; 424/64; 514/847; 514/873
[58] Field of Search ..................... 424/59, 60; 514/613

[56] References Cited

U.S. PATENT DOCUMENTS

| 3,816,611 | 6/1974 | Eberhardt et al. | 424/59 |
| 4,042,646 | 8/1977 | Edamura et al. | 525/46 |
| 4,178,449 | 12/1979 | Duisza et al. | 564/342 |

FOREIGN PATENT DOCUMENTS 0009609 4/1980 European Pat. Off. ............ 424/331

Primary Examiner—Dale R. Ore
Attorney, Agent, or Firm—Steven P. Berman

[57] ABSTRACT

Novel sunscreen compositions comprising at least one vinylogous amide compound are described as well as methods of protecting the human skin from damaging radiation.

7 Claims, No Drawings

SUNSCREEN COMPOSITIONS

CROSS REFERENCE TO RELATED APPLICATIONS

This application is a continuation-in-part of application Ser. No. 375,072 filed on May 5, 1982, now U.S. Pat. No. 4,514,383.

BACKGROUND OF THE INVENTION

This invention relates to new and useful ultraviolet radiation sunscreen agents and compositions and to methods of protecting the human skin against the potentially harmful effects of sunlight.

It is well documented that human skin is sensitive to sunlight containing radiation of wavelengths between about 290 nanometers (nm) and 400 nm as well as artificial light. Ultraviolet radiation of wavelengths between about 290 nm and 320 nm (UV-B region) has been known to rapidly produce damaging effects on the skin including reddening or erythema, edema, blistering or other skin eruptions in more severe cases. Prolonged or chronic exposure to radiation in this wavelength range has been associated with serious skin conditions such as actinic keratoses and carcinomas. In recent years concern has also been expressed regarding ultraviolet radiation of wavelengths above 320 nm (UV-A region) and the adverse effects of such radiation on human skin.

In view of the above, protection from the erythemal effects of sunlight produced by ultraviolet radiation within the UV-B region has been the traditional objective of sunscreen agents and compositions and as a result most compounds utilized as sunscreen agents have had light absorbance maxima within this UV-B region. Recently, as a result of growing concern for damage to the skin in the UV-A region, compounds capable of absorbing ultraviolet radiation in this region of the spectrum are becoming increasingly desirable but are generally unavailable.

Currently, the most widely utilized commercial sunscreen agents include para-amino benzoic acid derivatives, oxybenzones, methoxycinnamates and salicylates.

A desirable sunscreen agent should have absorbance maxima in the range of between 290 nm and 350 nm; have a molar absorptivity of greater than 10,000; be non-toxic, colorless and odorless; be heat and light stable; be water-insoluble and be easily and relatively inexpensively produced. While the readily available commercial sunscreen agents have enjoyed a measure of success, they all lack one or more of the above desirable properties.

OBJECTS OF THE INVENTION

It is an object of the present invention to provide improved sunscreen agents and compositions.

It is another object of the present invention to provide sunscreen compositions containing sunscreen agents that overcome the disadvantages of heretofore available materials and provide adequate and safe protection for human skin.

It is a further object of this invention to provide methods of protecting human skin against the harmful effects of sunlight.

These and other objects and features of the present invention will become readily apparent to one skilled in the art from the detailed description given hereinafter.

SUMMARY OF THE INVENTION

The foregoing objects and other features and advantages of the present invention are achieved by sunscreen compositions containing one or more vinylogous amides as the sunscreen agent.

DETAILED DESCRIPTION OF THE INVENTION

The sunscreen compositions of the present invention contain as an active sunscreen agent at least one vinylogous amide compound of the formula

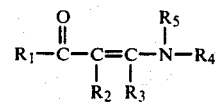

wherein
$R_1$ is selected from alkyl, cycloalkyl, alkenyl, cycloalkenyl, aryl, substituted aryl or alkaryl of from 1 to 18 carbon atoms;
$R_2$ and $R_3$ may be the same or different and are selected from hydrogen, alkyl, alkenyl, cycloalkyl or cycloalkenyl of from 1 to 18 carbon atoms;
$R_4$ and $R_5$ may be the same or different and are selected from hydrogen, alkyl, alkenyl, aryl and substituted aryl, alkaryl, cycloalkyl or cycloalkenyl of from 1 to 18 carbon atoms; provided that at least one of $R_1$, $R_2$, $R_3$, $R_4$, or $R_5$ is interrupted or substituted by N or O. When N is present it may be as a primary, secondary, or tertiary amine, quaternary ammonium salt, or amide. When O is present it may be as an alcohol, carboxylic acid or ester, or ether. $R_2$ together with $R_1$ and/or $R_3$ may form carbocyclic and/or heterocyclic rings, and $R_4$ together with $R_5$ may form heterocyclic rings.

The vinylogous amides useful in the present invention can be prepared by mixing equivalent amounts of a suitable amine with a suitable β-dicarbonyl compound. This may be done without solvent or with an appropriate amount of a solvent such as lower alcohols, toluene, water or the like. The reaction may require heating, usually at 50° C. to 80° C., for a period of time to complete the reaction.

The vinylogous amides described above include all cis-trans positional isomers thereof.

Specific examples of vinylogous amides which are useful in the present invention include:

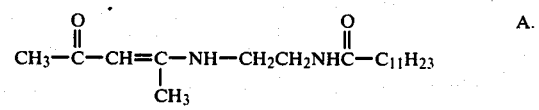

A.

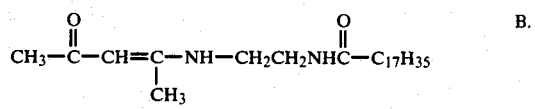

B.

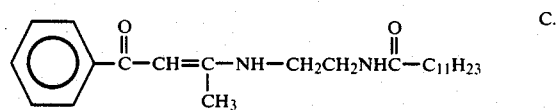

C.

3

-continued

D. CH₃-C(=O)-C(CH₃)=C(CH₃)-NH-CH₂CH₂-NHC(=O)-C₁₁H₂₃

E. CH₃CH₂-C(=O)-C(C₄H₉)=C(CH₃)-NH-CH₂CH₂OH

F. CH₃-C(=O)-C(CH(CH₃)₂)=C(CH₃)-NHCH₂-CHOH-CH₂OH

G. CH₃-C(=O)-CH=C(CH₂OCH₃)-NH-C₁₂H₂₅

H. C₁₁H₂₃C(=O)-CH=C(CH₃)-N(CH₂CH₂OH)(CH₂CH₂OH)

I. C₁₇H₃₅C(=O)-CH=C(CH₃)-N(morpholine)

J. C₁₁H₂₃-C(=O)-CH=C(CH₃)-N(piperazine-NH)

K. CH₃-C(=O)-CH=C(CH₃)-N⁺(piperazinium-CH₃)-C₁₁H₂₃ Cl⁻

L. CH₃-C(=O)-CH=C(CH₃)-NH-(CH₂)₆-NH₂

M. CH₃-C(=O)-CH=C(CH₃)-NH-(CH₂)₆NHC(=O)-CH₃

N. CH₃-C(=O)-CH=C(CH₃)-NH-(CH₂)₆-OH

O. CH₃-C(=O)-CH=C(CH₃)-NH-(CH₂)₆-OC(=O)-CH=C(CH₃)-NH-CH₃

P. CH₃-C(=O)-CH=C(CH₃)-NH-(CH₂)₆-NHC(=O)-CH=C(CH₃)-NH-CH₃

Q. CH₃-C(=O)-CH=C(CH₃)-NHCH₂CH₂O-C(=O)-C₁₁H₂₃

4

-continued

R. CH₃-C(=O)-CH=C(CH₃)-NH-C₆H₄-CO₂-CH₂CH₃

S. CH₃-C(=O)-CH=C(CH₃)-NH-(CH₂)₆-NH-C(CH₃)=CH-C(=O)-CH₃

T. CH₃-C(=O)-CH=C(CH₃)-NH-C(=O)-C₁₁H₂₃

U. CH₃-C(=O)-CH=C(CH₃)-NH-C(=O)-NH-CH₃

V. CH₃-C(=O)-CH=C(CH₃)-NH-CH₂CH₂O-CH₂CH₂OH

W. CH₃-C(=O)-CH=C(CH₃)-NH-CH₂CH₂NH-CH₂CH₂OH

X. CH₃-C(=O)-CH=C(CH₃)-NH-CH₂CH₂CH₂O-C₁₂H₂₅

Y. CH₃C(=O)-CH=C(CH₃)-NH-(CH₂)₃NH(CH₂)₃-O-C₁₂H₂₅

Z. CH₃-C(=O)-CH=C(CH₃)-NH-(CH₂)₃NH-C₁₂H₂₅

AA. CH₃C(=O)-CH=C(CH₃)-NH-(CH₂)₃-N⁺(CH₂CH₃)(CH₂CH₃)-C₄H₉ Br⁻

BB. CH₃-C(=O)-CH=C(CH₃)-NH-CH₂CH₂CH₂N(CH₃)₂

CC. CH₃C(=O)-CH=C(CH₃)-NH-CH₂CO₂CH₂CH₃

DD. CH₃C(=O)-CH=C(CH₃)-NH-CH₂-CO₂H

EE. (2-furyl)-C(=O)-CH=C(CH₃)-NH-C₁₂H₂₅

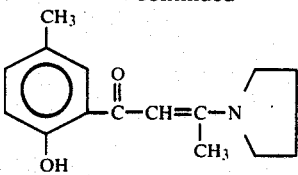

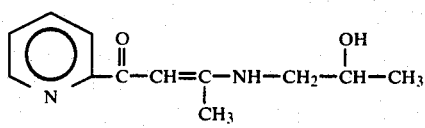 GG.

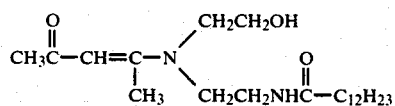 HH.

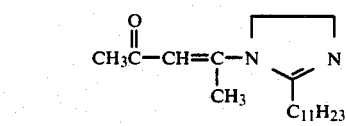 II.

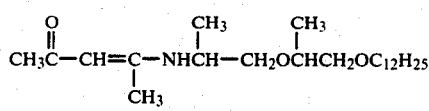 JJ.

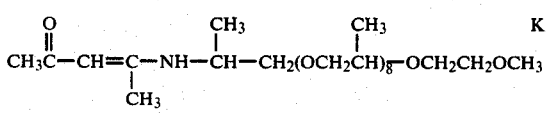 KK.

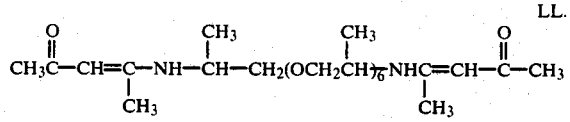 LL.

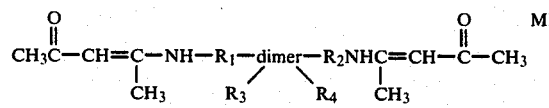 MM.

(bis-3-pentene-2-one derivative of fatty dimer amine)

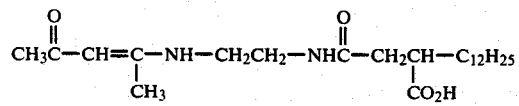 NN.

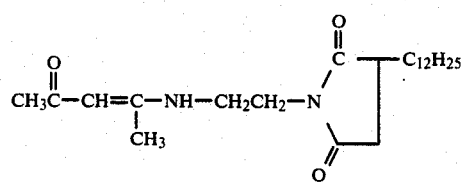 OO.

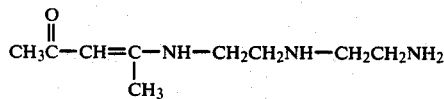 PP.

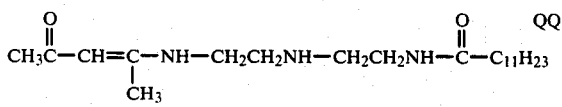 QQ.

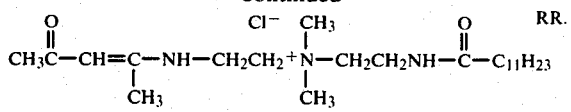 FF.

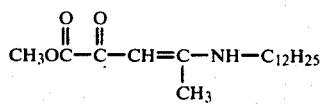 RR.

SS.

$$CH_3OC-C-CH=C-NH-C_{12}H_{25}$$
$$\phantom{CH_3OC-C-CH=}CH_3$$

The vinylogous amides useful in the formulations of the present invention exhibit light absorbance maxima in either the UV-A or UV-B regions and thus depending on the choice of specific vinylogous amides one can formulate compositions which are effective sunscreens in either of these regions or by selecting a mixture of said vinylogous amides in both regions of the spectrum. It is also possible and may sometimes be desirable to combine the vinylogous amide sunscreen agents with conventional sunscreen agents to form effective sunscreen compositions. Such conventional sunscreen agents include Padimate O (2-ethylhexyl-p-dimethylaminobenzoate), oxybenzone, salicylates and the like.

The sunscreen compositions of the present invention contain the sunscreen agent or combination of sunscreen agents and a pharmaceutically extending medium such as a carrier or vehicle which adapts said agents for application to the skin. These compositions can be in either solid, liquid or aerosol form. The sunscreen agents of the present invention can also be incorporated into various cosmetic and personal care products such as hand and body lotions, oils, ointments, lip balm products, facial cosmetics and the like.

The amount of sunscreen agent present in the sunscreen compositions or the cosmetic and personal care products may vary greatly but is preferable in a range of about 1 to 20% by weight of the total composition. One or more sunscreen agents may be utilized with the combined concentration of said agents preferably in the range of 1 to 20% by weight of the composition. Greater amounts of these agents may be incorporated into various products limited only by processing and economic considerations.

Specific embodiments of the present invention are illustrated by the following examples. It will be understood, however, that the invention is not confined to the specific limitations set forth in the individual examples, but rather to the scope of the appended claims.

EXAMPLE I

Preparation of Compound (A)

In a suitable reactor equipped with heating, stirring and reflux facilities are combined under nitrogen atmosphere 100.12 g of pentane-2,4-dione (1.0 mole), 242.08 of aminoethyl lauramide (1.0 mole) and 500 ml methanol. The mixture is heated at the boil for two hours. Removal of the solvent yields 324 g of a compound of the formula

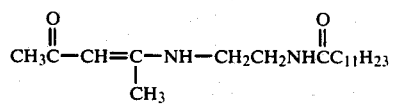

EXAMPLE II

Preparation of Compound (C)

In the reactor of Example I are combined 162.0 g of benzoyl acetone (1.0 mole), 242.0 g of aminoethyl lauramide (1.0 mole) and 700 ml of toluene. The mixture is heated at 80° C. for one hour. After removal of the solvent, there remains 386.0 g of a compound of the formula

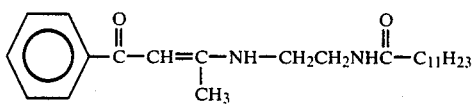

EXAMPLE III

Preparation of Compound (E)

In the reactor of Example I are combined 170.0 g of 3-propionyl-2-heptanone (1.0 l mole), 61.0 g ethanolamine (1.0 mole) and 500 ml methanol. The mixture is heated at the boil for two hours. Removal of the solvent produces 213.0 g of a compound of the formula

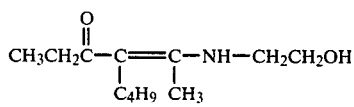

EXAMPLE IV

Preparation of Compound (G)

In a suitable eactor are combined 13.0 g of 1-methoxy-2,4-pentanedione (0.1 mole) and 18.5 g of dodecylamine (0.1 mole). After sufficient heating to melt the reagents, the mixture is heated to 50° C. over a ten minute period. After one hour the mixture cools and yields 29.7 g of a compound of the formula

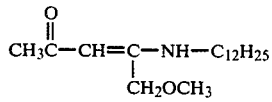

EXAMPLE V

Preparation of Compound (I)

In a suitable reactor are combined 32.4 g of stearoyl acetone (0.1 mole), 8.7 g of morpholine (0.1 mole) and 100 ml of methanol. The mixture is heated at the boil for two hours. Removal of the solvent produces a compound of formula

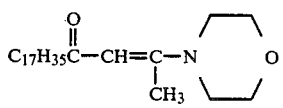

EXAMPLE VI

Preparation of Compound (N)

In a suitable reactor are combined 100.12 g of pentane-2,4-dione (1.0 mole), 117.0 g of 6-amino-1-hexanol (1.0 mole) and 300 ml of methanol. The mixture is heated at the boil for two hours. Removal of the solvent yields 199.0 g of a compound of the formula

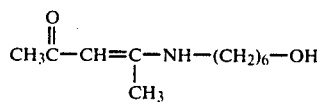

EXAMPLE VII

Preparation of Compound (O)

19.9 g (0.1 mole) of the product of Example VI in 200 ml of methylene chloride is treated by the gradual addition of 8.4 g (0.1 mole) diketene. When the reaction is complete, 3.1 g methylamine (0.1 mole) is added and the mixture is heated at the boil for two hours. Removal of the solvent yields a compound of the formula

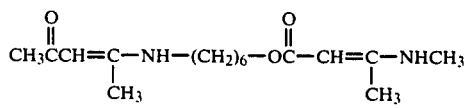

EXAMPLE VIII

Preparation of Compound (DD)

In a suitable reactor are combined 100.12 g of pentane-2,4-dione (1.0 mole), 75.0 g of glycine (1.0 mole) and 500 ml of water. The mixture is stirred at 60° C. and the pH maintained near 8 unitl the pH is stable. The mixture is cooled, acidified to pH 3, and evaporated to yield a compound of the formula

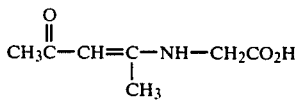

EXAMPLE IX

Preparation of Compound (HH)

In a suitable reactor are combined 100.12 g of pentane-2,4-dione (1.0 mole), 286.0 g of the condensation product of lauric acid with aminoethyl ethanolamine (1.0 mole) and 1000 ml of methanol. The mixture is heated at the boil for four hours. Removal of the solvent yields a compound of the formula

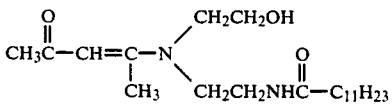

EXAMPLE X

A sunscreen formulation is prepared according to the following procedure. In a suitable beaker, with vigorous agitation, 1.50 g of Carbopol 941 thickening agent, 0.25 g disodium ethylenediamine tetraacetate (disodium EDTA) preservative and chelating agent, 1.00 g Methocel K100LV stabilizer and 0.65 g Kthon CG preservative are added to 354.1 g of deionized water and heated to 70° C. 15.00 g of a 7.5% solution of ammonium hydroxide ae added and mixing continues for 5 minutes. In a second beaker, 5.00 g stearyl alcohol emollient, 10.00 g Emerest 2400 emollient, 10.00 g mineral oil emollient, 2.50 g dimethicone emollient, 25.00 g Finsolv TN emollient and 15.00 g isostearic acid emulsifier are heated to 70° C. In a third beaker, 25.00 g of Compound A and 15.00 g of Compound C are premelted at 70° C. and then added to the contents in the second beaker and mixed for five minutes at 70° C. The contents of the second beaker are then added to the first beaker and the resulting emulsion is cooled to 50° C., homogenized, and cooled to room temperature.

The resulting composition is an emulsion which is an opaque, free flowing lotion.

The resulting composition has the following formulation:

| Ingredient | % by wt. |
|---|---|
| Carbopol 941 (B. F. Goodrich's tradename for carboxy vinyl polymer) | 0.30 |
| disodium EDTA | 0.05 |
| Methocel K100LV (Dow Chemical's tradename for hydroxypropyl methylcellulose) | 0.20 |
| Kathon CG (Rohm & Haas' tradename for methyl- and methylchloro-isothiazolinones) | 0.13 |
| ammonium hydroxide (7.5%) | 3.00 |
| stearyl alcohol | 1.00 |
| Emerest 2400 (Emery Industries tradename for glyceryl stearate) | 2.00 |
| mineral oil | 2.00 |
| isostearic acid | 3.00 |
| dimethicone, 50 cs. | 0.50 |
| Finsolv TN (Finetex's tradename for $C_{12}$-$C_{15}$ alcohol benzoates) | 5.00 |
| Compound A | 5.00 |
| Compound C | 3.00 |
| deionized water | balance to 100.00 |

EXAMPLE XI

A sunscreen composition is prepared in accordance with the procedure of Example X and consists of the following ingredients:

| Ingredient | % by wt. |
|---|---|
| Carbopol 934 (B. F. Goodrich's tradename for carboxy vinyl polymer) | 0.30 |
| disodium EDTA | 0.05 |
| Methocel J40MS (Dow Chemical's tradename for hydroxypropyl methylcellulose) | 0.50 |
| Kathon CG | 0.13 |
| ammonium hydroxide (7.5%) | 3.00 |
| stearyl alcohol | 1.00 |
| Emerest 2400 | 2.00 |
| mineral oil | 2.00 |
| isostearic acid | 3.00 |
| dimethicone, 50 cs. | 0.50 |
| Finsolv TN | 5.00 |
| BHT (trade usage for butylated hydroxytoluene) | 0.05 |
| Compound E | 5.00 |
| Compound C | 3.00 |
| deionized water | balance to 100.00 |

The resulting composition is a white, opaque lotion.

EXAMPLE XII

A sunscreen composition is prepared in accordance with the procedure of Example X and consists of the following ingredients:

| Ingredient | % by wt. |
|---|---|
| Carbopol 934 | 0.30 |
| disodium EDTA | 0.05 |
| Methocel J40MS | 0.50 |
| Kathon CG | 0.13 |
| ammonium hydroxide (7.5%) | 3.00 |
| stearyl alcohol | 1.00 |
| Emerest 2400 | 2.00 |
| mineral oil | 2.00 |
| isostearic acid | 3.00 |
| dimethicone, 50 cs. | 0.50 |
| Finsolv TN | 5.00 |
| BHT | 0.05 |
| Compound G | 5.00 |
| deionized water | balance to 100.00 |

The resulting composition is a white, opaque lotion.

EXAMPLE XIII

A sunscreen composition is prepared in accordance with the procedure of Example X and consists of the following ingredients:

| Ingredient | % by wt. |
|---|---|
| Carbopol 934 | 0.30 |
| disodium EDTA | 0.05 |
| Methocel J40MS | 0.50 |
| Kathon CG | 0.13 |
| ammonium hydroxide (7.5%) | 3.00 |
| stearyl alcohol | 1.00 |
| Emerest 2400 | 2.00 |
| mineral oil | 2.00 |
| isostearic acid | 3.00 |
| dimethicone, 50 cs. | 0.50 |
| Finsolv TN | 5.00 |
| BHT | 0.05 |
| Compound A | 5.00 |
| Padimate O | 4.00 |
| deionized water | balance to 100.00 |

The resulting composition is a white, opaque lotion.

EXAMPLE XIV

A sunscreen composition is prepared in accordance with the procedure of Example V and consists of the following ingredients:

| Ingredient | % by wt. |
|---|---|
| Carbopol 934 | 0.30 |
| disodium EDTA | 0.05 |
| Methocel J40MS | 0.50 |
| Kathon CG | 0.13 |
| ammonium hydroxide (7.5%) | 3.00 |
| stearyl alcohol | 1.00 |
| Emerest 2400 | 2.00 |
| mineral oil | 2.00 |
| isostearic acid | 3.00 |
| dimethicone, 50 cs. | 0.50 |
| Finsolv TN | 5.00 |
| BHT | 0.05 |
| Compound I | 7.00 |
| deionized water | balance to 100.00 |

The resulting composition is a white, opaque lotion.

EXAMPLE XV

A sunscreen composition is prepared in accordance with the procedure of Example X and consists of the following ingredients:

| Ingredient | % by wt. |
| --- | --- |
| Carbopol 934 | 0.30 |
| disodium EDTA | 0.05 |
| Methocel J40MS | 0.50 |
| Kathon CG | 0.13 |
| ammonium hydroxide (7.5%) | 3.00 |
| stearyl alcohol | 1.00 |
| Emerest 2400 | 2.00 |
| mineral oil | 2.00 |
| isostearic acid | 3.00 |
| dimethicone, 50 cs. | 0.50 |
| Finsolv TN | 5.00 |
| BHT | 0.05 |
| Compound O | 8.00 |
| deionized water | balance to 100.00 |

The resulting composition is a white, opaque lotion.

EXAMPLE XVI

A sunscreen composition is prepared in accordance with the procedure of Example X and consists of the following ingredients:

| Ingredient | % by wt. |
| --- | --- |
| Carbopol 934 | 0.30 |
| disodium EDTA | 0.05 |
| Methocel J40MS | 0.50 |
| Kathon CG | 0.13 |
| ammonium hydroxide (7.5%) | 3.00 |
| stearyl alcohol | 1.00 |
| Emerest 2400 | 2.00 |
| mineral oil | 2.00 |
| isostearic acid | 3.00 |
| dimethicone, 50 cs. | 0.50 |
| Finsolv TN | 5.00 |
| BHT | 0.05 |
| Compound HH | 5.00 |
| Padimate O | 3.00 |
| deionized water | balance to 100.00 |

The resulting composition is a white, opaque lotion.

EXAMPLE XVII

A hand and body lotion composition is prepared as follows:

In a suitable beaker with vigorous agitation, 3.0 g of Carbopol 934 and 40 g propylene glycol are added to 788.7 g deionized water and heated to 70° C. In a second beaker, 10 g isopropylpalmitate, 10.0 g dimethicone (50 cs), 12.5 g oleic acid, 10.0 g stearoxymethylsilane, 8.0 g sorbitan stearate, 5.0 g cetyl alcohol, 5.0 g stearyl alcohol, 5.0 g synthetic beeswax, 12.5 g glyceryl monostearate, 12.5 g stearic acid, 12.0 g polysorbate 61, 15.0 g myristyl myristate, 2.0 g BHT and 3.0 g benzyl alcohol are melted. The contents of the second beaker are added to the contents of the first beaker and to the resultant mixture are added 0.5 g butylparaben, 1.0 g propylparaben and 1.5 g methylparaben followed by the addition of 2.6 g of a 50% solution of sodium hydroxide, 20.0 g of Compound A and 20.0 g of Compound C. The resulting emulsion is homogenized and cooled to 45° C. at which point 2.0 g of fragrance are added followed by cooling to room temperature resulting in a thick, white lotion.

The resulting composition has the following formulation:

| Ingredients | % by wt. |
| --- | --- |
| Carbopol 934 | 0.30 |
| propylene glycol | 4.00 |
| isopropyl palmitate | 1.00 |
| dimethicone, 50 cs. | 1.00 |
| oleic acid | 1.25 |
| stearoxymethylsilane | 1.00 |
| sorbitan stearate | 0.80 |
| cetyl alcohol | 0.50 |
| stearyl alcohol | 0.50 |
| synthetic beeswax | 0.50 |
| glyceryl monostearate | 1.25 |
| stearic acid | 1.25 |
| polysorbate 61 | 1.20 |
| myristyl myristate | 1.50 |
| butylparaben | 0.05 |
| propylparaben | 0.10 |
| methylparaben | 0.15 |
| BHT | 0.02 |
| sodium hydroxide (50%) | 0.26 |
| benzyl alcohol | 0.30 |
| fragrance | 0.20 |
| Compound A | 2.00 |
| Compound C | 2.00 |
| deionized water | balance to 100.00 |

EXAMPLE XVIII

A lotion formulation is prepared according to the procedure of Example XVII and consists of the following ingredients:

| Ingredients | % by wt. |
| --- | --- |
| Carbopol 934 | 0.30 |
| propylene glycol | 4.00 |
| isopropyl palmitate | 1.00 |
| dimethicone, 50 cs. | 1.00 |
| oleic acid | 1.25 |
| stearoxymethylsilane | 1.00 |
| sorbitan stearate | 0.80 |
| cetyl alcohol | 0.50 |
| stearyl alcohol | 0.50 |
| synthetic beeswax | 0.50 |
| glyceryl monostearate | 1.25 |
| stearic acid | 1.25 |
| polysorbate 61 | 1.20 |
| myristyl myristate | 1.50 |
| butylparaben | 0.05 |
| propylparaben | 0.10 |
| methylparaben | 0.15 |
| BHT | 0.02 |
| sodium hydroxide (50%) | 0.26 |
| benzyl alcohol | 0.30 |
| fragrance | 0.20 |
| Padimate O | 4.00 |
| Compound C | 3.00 |
| deionized water | balance to 100.00 |

The resulting composition is a thick, white lotion.

EXAMPLE XIX

A lotion formulation is prepared according to the procedure of Example XVII and consists of the following ingredients:

| Ingredients | % by wt. |
| --- | --- |
| Carbopol 934 | 0.30 |
| propylene glycol | 4.00 |
| isopropyl palmitate | 1.00 |
| dimethicone, 50 cs. | 1.00 |
| oleic acid | 1.25 |
| stearoxymethylsilane | 1.00 |
| sorbitan stearate | 0.80 |
| cetyl alcohol | 0.50 |
| stearyl alcohol | 0.50 |

-continued

| Ingredients | % by wt. |
| --- | --- |
| synthetic beeswax | 0.50 |
| glyceryl monostearate | 1.25 |
| stearic acid | 1.25 |
| polysorbate 61 | 1.20 |
| myristyl myristate | 1.50 |
| butylparaben | 0.05 |
| propylparaben | 0.10 |
| methylparaben | 0.15 |
| BHT | 0.02 |
| sodium hydroxide (50%) | 0.26 |
| benzyl alcohol | 0.30 |
| fragrance | 0.20 |
| octyl salicylate | 2.00 |
| Compound E | 2.00 |
| deionized water | balance to 100.00 |

The resulting composition is a thick, white lotion.

EXAMPLE XX

A lotion formulation is prepared according to the procedure of Example XVII and consists of the following ingredients:

| Ingredients | % by wt. |
| --- | --- |
| Carbopol 934 | 0.30 |
| propylene glycol | 4.00 |
| isopropyl palmitate | 1.00 |
| dimethicone, 50 cs. | 1.00 |
| oleic acid | 1.25 |
| stearoxymethylsilane | 1.00 |
| sorbitan stearate | 0.80 |
| cetyl alcohol | 0.50 |
| stearyl alcohol | 0.50 |
| synthetic beeswax | 0.50 |
| glyceryl monostearate | 1.25 |
| stearic acid | 1.25 |
| polysorbate 61 | 1.20 |
| butylparaben | 0.05 |
| propylparaben | 0.10 |
| methylparaben | 0.15 |
| BHT | 0.02 |
| sodium hydroxide (50%) | 0.26 |
| benzyl alcohol | 0.30 |
| fragrance | 0.20 |
| Compound O | 4.00 |
| deionized water | balance to 100.00 |

The resulting composition is a thick, white lotion.

EXAMPLE XXI

A lotion formulation is prepared according to the procedure of Example XVII and consists of the following ingredients:

| Ingredients | % by wt. |
| --- | --- |
| Carbopol 934 | 0.30 |
| propylene glycol | 4.00 |
| isopropyl palmitate | 1.00 |
| dimethicone, 50 cs. | 1.00 |
| oleic acid | 1.25 |
| stearoxymethylsilane | 1.00 |
| sorbitan stearate | 0.80 |
| cetyl alcohol | 0.50 |
| stearyl alcohol | 0.50 |
| synthetic beeswax | 0.50 |
| glyceryl monostearate | 1.25 |
| stearic acid | 1.25 |
| polysorbate 61 | 1.20 |
| butylparaben | 0.05 |
| propylparaben | 0.10 |
| methylparaben | 0.15 |
| BHT | 0.02 |
| sodium hydroxide (50%) | 0.26 |

-continued

| Ingredients | % by wt. |
| --- | --- |
| benzyl alcohol | 0.30 |
| fragrance | 0.20 |
| Compound I | 2.00 |
| Compound DD | 2.00 |
| deionized water | balance to 100.00 |

The resulting composition is a thick, white lotion.

EXAMPLE XXII

A hand cream composition is prepared according to the following procedure. In a suitable beaker 367.4 g mineral oil, 55.0 g lanolin, 80.0 g white wax, 45.7 g paraffin, 70.0 g synthetic beeswax, 10.0 g glyceryl monostearate and 68.5 g white ceresine wax are melted and kept at a temperature of 70° C. In a second beaker 241.8 g of deionized water, 9.0 g powdered borax and 1.0 g propylparaben are heated to 70° C. and the contents of the first beaker are added to the second beaker and 30 g of Compound A and 20.0 g of Compound C are added thereto. The mixture is cooled to 55° C. and 1.6 g of fragrance are added and the cooling continued to 45° C. and the resulting composition filled in a suitable container and cooled to room temperature.

The resulting composition has the following formulation:

| Ingredients | % by wt. |
| --- | --- |
| mineral oil | 36.74 |
| lanolin, anhydrous cosmetic grade | 5.50 |
| white wax, USP | 8.00 |
| paraffin | 4.57 |
| synthetic beeswax | 7.00 |
| glyceryl monostearate | 1.00 |
| white ceresine wax | 6.85 |
| powdered borax | 0.90 |
| fragrance | 0.16 |
| propylparaben | 0.10 |
| Compound A | 3.00 |
| Compound C | 2.00 |
| deionized water | balance to 100.00 |

EXAMPLE XXIII

A hand cream formulation is prepared according to the procedure of Example XXII and consists of the following ingredients:

| Ingredients | % by wt. |
| --- | --- |
| mineral oil | 36.74 |
| lanolin, anhydrous cosmetic grade | 5.50 |
| white wax, USP | 8.00 |
| paraffin | 4.57 |
| synthetic beeswax | 7.00 |
| glyceryl monostearate | 1.00 |
| white ceresine wax | 6.85 |
| powdered borax | 0.90 |
| fragrance | 0.16 |
| propylparaben | 0.10 |
| Compound AA | 3.00 |
| deionized water | balance to 100.00 |

EXAMPLE XIV

A hand cream formulation is prepared according to the procedure of Example XXII and consists of the following ingredients:

| Ingredients | % by wt. |
|---|---|
| mineral oil | 36.74 |
| lanolin, anhydrous cosmetic grade | 5.50 |
| white wax, USP | 8.00 |
| paraffin | 4.57 |
| synthetic beeswax | 7.00 |
| glyceryl monostearate | 1.00 |
| white ceresine wax | 6.85 |
| powdered borax | 0.90 |
| fragrance | 0.16 |
| propylparaben | 0.10 |
| Compound O | 3.00 |
| deionized water | balance to 100.00 |

EXAMPLE XXV

A hand cream formulation is prepared according to the procedure of Example XXII and consists of the following ingredients:

| Ingredients | % by wt. |
|---|---|
| mineral oil | 36.74 |
| lanolin, anhydrous cosmetic grade | 5.50 |
| white wax, USP | 8.00 |
| paraffin | 4.57 |
| synthetic beeswax | 7.00 |
| glyceryl monostearate | 1.00 |
| white ceresine wax | 6.85 |
| powdered borax | 0.90 |
| fragrance | 0.16 |
| propylparaben | 0.10 |
| octyl salicylate | 4.00 |
| Compound R | 3.00 |
| deionized water | balance to 100.00 |

EXAMPLE XXVI

A hand cream formulation is prepared according to the procedure of Example XXII and consists of the following ingredients:

| Ingredients | % by wt. |
|---|---|
| mineral oil | 36.74 |
| lanolin, anhydrous cosmetic grade | 5.50 |
| white wax, USP | 8.00 |
| paraffin | 4.57 |
| synthetic beeswax | 7.00 |
| glyceryl monostearate | 1.00 |
| white ceresine wax | 6.85 |
| powdered borax | 0.90 |
| fragrance | 0.16 |
| propylparaben | 0.10 |
| Compound JJ | 2.00 |
| deionized water | balance to 100.00 |

EXAMPLE XXVII

A dry skin composition is prepared in accordance with the following procedure. In a suitable beaker 450.0 g petrolatum, 30.0 g polyethylene and 20.0 g silicon dioxide are melted at 80° C. and homogenized. To this mixture, 338.0 g cyclomethicone, 100.0 g dimethicone, 10.0 g mineral oil, 1.0 g propylparaben, 1.0 g sorbic acid and 50.0 g Compound Q are added and the resultant mixture is cooled to 35° C.

The resulting composition has the following formulation:

| Ingredients | % by wt. |
|---|---|
| petrolatum, white USP | 45.0 |
| polyethylene | 3.0 |
| silicon dioxide | 2.0 |
| cyclomethicone | 33.8 |
| dimethicone, 50 cs. | 10.0 |
| mineral oil | 1.0 |
| propylparaben | 0.1 |
| sorbic acid | 0.1 |
| Compound Q | 5.0 |
| | 100.0 |

EXAMPLE XVIII

A dry skin formulation is prepared according to the procedure of Example XXVII and consists of the following ingredients:

| Ingredients | % by wt. |
|---|---|
| petrolatum, white USP | 49.0 |
| polyethylene | 3.0 |
| silicon dioxide | 2.0 |
| cyclomethicone | 33.8 |
| dimethicone, 50 cs. | 10.0 |
| mineral oil | 1.0 |
| propylparaben | 0.1 |
| sorbic acid | 0.1 |
| Compound MM | 5.0 |
| | 100.0 |

EXAMPLE XXIX

A dry skin formulation is prepared according to the procedure of Example XXVII and consists of the following ingredients:

| Ingredients | % by wt. |
|---|---|
| petrolatum, white USP | 45.0 |
| polyethylene | 3.0 |
| silicon dioxide | 2.0 |
| cyclomethicone | 33.8 |
| dimethicone, 50 cs. | 10.0 |
| mineral oil, J & J Special | 1.0 |
| propylparaben | 0.1 |
| sorbic acid | 0.1 |
| Padimate O | 3.0 |
| Compound C | 2.0 |
| | 100.0 |

EXAMPLE XXX

A dry skin formulation is prepared according to the procedure of Example XXVII and consists of the following ingredients:

| Ingredients | % by wt. |
|---|---|
| petrolatum, white USP | 45.0 |
| polyethylene | 3.0 |
| silicon dioxide | 2.0 |
| cyclomethicone | 33.8 |
| dimethicone, 50 cs. | 10.0 |
| mineral oil | 1.0 |
| propylparaben | 0.1 |
| sorbic acid | 0.1 |
| oxybenzone | 2.0 |
| Compound B | 3.0 |
| | 100.0 |

EXAMPLE XXXI

A lip balm composition is prepared according to the following procedure. In a suitable beaker 72.0 g petrolatum, 8.0 g Syncrowax HRC, 8.0 g Syncrowax ERL-C, 8.0 g Syncrowax HGL-C, 2.0 g Compound B and 2.0 g oxybenzone are added. The mixture is melted and cast into sticks at a temperature of 60° C.

The resulting composition has the following formulation:

| Ingredients | % by wt. |
| --- | --- |
| petrolatum, white USP | 72.0 |
| Syncrowax HRC (Croda's tradename for glyceryl tribehenate) | 8.0 |
| Syncrowax ERL-C (Croda's tradename for $C_{18}$–$C_{36}$ wax fatty acid ethylene glycol ester) | 8.0 |
| Syncrowax HGL-C (Croda's tradename for $C_{18}$–$C_{36}$ wax fatty acid triglyceride) | 8.0 |
| Compound B | 2.0 |
| oxybenzone | 2.0 |
|  | 100.0 |

EXAMPLE XXXII

A lip balm composition is prepared according to the procedure of Example XXXI and consists of the following ingredients:

| Ingredients | % by wt. |
| --- | --- |
| petrolatum, white USP | 69.0 |
| Syncrowax HRC | 8.0 |
| Syncrowax ERL-C | 8.0 |
| Syncrowax HGL-C | 8.0 |
| Compound A | 4.0 |
| Compound C | 3.0 |
|  | 100.0 |

EXAMPLE XXXIII

A lip balm composition is prepared according to the procedure of Example XXXI and consists of the following ingredients:

| Ingredients | % by wt. |
| --- | --- |
| petrolatum, white USP | 70.0 |
| Syncrowax HRC | 8.0 |
| Syncrowax ERL-C | 8.0 |
| Syncrowax HGL-C | 8.0 |
| Compound M | 2.0 |
| Padimate O | 4.0 |
|  | 100.0 |

EXAMPLE XXXIV

A lip balm composition is prepared according to the procedure of Example XXXI and consists of the following ingredients:

| Ingredients | % by wt. |
| --- | --- |
| petrolatum, white USP | 74.0 |
| Syncrowax HRC | 8.0 |
| Syncrowax ERL-C | 8.0 |
| Syncrowax HGL-C | 8.0 |
| octyl salicylate | 1.0 |
| Compound HH | 1.0 |

| Ingredients | % by wt. |
| --- | --- |
|  | 100.0 |

What is claimed is:

1. A sunscreen composition comprising an extending medium and from about 1 to 20% by weight of the total composition of at least one vinylogous amide compound of the formula

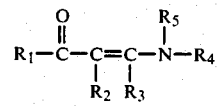

wherein
- $R_1$ is selected from alkyl, cycloalkyl, alkenyl, cycloalkenyl, aryl, substituted aryl or alkaryl of from 1 to 18 carbon atoms;
- $R_2$ and $R_3$ are the same or different and are selected from hydrogen, alkyl, alkenyl, cycloalkyl or cycloalkenyl of from 1 to 18 carbon atoms;
- $R_4$ and $R_5$ are the same or different and are selected from hydrogen, alkyl, alkenyl, aryl and substituted aryl, alkaryl, cycloalkyl or cycloalkenyl of from 1 to 18 carbon atoms;
- provided that at least one of $R_4$ or $R_5$ is interrupted or substituted by N;
- wherein when N is present it is an amide;
- and furthermore wherein $R_2$ together with $R_1$ and/or $R_3$ may form carbocyclic rings and $R_4$ together with $R_5$ may form heterocyclic rings.

2. The composition of claim 1 wherein the vinylogous amide is of the formula

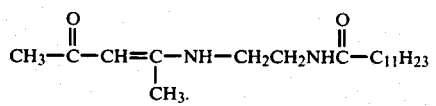

3. The composition of claim 1 wherein the vinylogous amide is of the formula

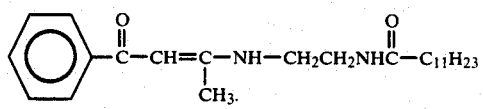

4. The composition of claim 1 wherein the vinylogous amide is present from about 1 to 20% by weight of the total composition.

5. The composition of claim 1 containing at least one vinylogous amide and in addition oxybenzone.

6. The composition of claim 1 containing at least one vinylogous amide and in addition 2-ethylhexyl-p-dimethylaminobenzoate.

7. A method of protecting human skin from the erythmic effects of ultraviolet radiation which comprises applying to the skin a sunscreen composition containing an extending medium and from about 1 to 20% by weight of the total composition of at least one vinylogous amide compound of the formula

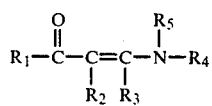

wherein

R₁ is selected from alkyl, cycloalkyl, alkenyl, cycloalkenyl, aryl, substituted aryl or alkaryl of from 1 to 18 carbon atoms;

$R_2$ and $R_3$ are the same or different and are selected from hydrogen, alkyl, alkenyl, cycloalkyl or cycloalkenyl of from 1 to 18 carbon atoms;

$R_4$ and $R_5$ are the same or different and are selected from hydrogen, alkyl, alkenyl, aryl and substituted aryl, alkaryl, cycloalkyl or cycloalkenyl or from 1 to 18 carbon atoms;

provided that at least one of $R_4$ or $R_5$ is interrupted or substituted by N;

wherein when N is present it is an amide;

and furthermore wherein $R_2$ together with $R_1$ and/or $R_3$ may form carbocyclic rings and $R_4$ together with $R_5$ may form heterocyclic rings.

* * * * *